United States Patent [19]
Dadd et al.

[11] Patent Number: 5,688,912
[45] Date of Patent: Nov. 18, 1997

[54] PEPTIDE LIGANDS WHICH BIND TO VON WILLEBRAND FACTOR

[75] Inventors: Christopher A. Dadd, Cary; George A. Baumbach, Knightdale; David J. Hammond, Raleigh, all of N.C.

[73] Assignee: Bayer Corporation, Berkeley, Calif.

[21] Appl. No.: 537,069

[22] Filed: Sep. 22, 1995

[51] Int. Cl.$^6$ .............. C07K 7/04; C07K 17/00; A61K 35/14
[52] U.S. Cl. .............. 530/329; 530/381; 530/413; 530/383
[58] Field of Search .............. 530/329, 381, 530/413, 383

[56] References Cited

U.S. PATENT DOCUMENTS

5,110,907  5/1992  Kosow et al. .............. 530/383
5,200,510  4/1993  Kumar et al. .............. 530/383

Primary Examiner—Cecilia J. Tsang
Assistant Examiner—Michael L. Borin
Attorney, Agent, or Firm—James A. Giblin; Michael J. Beck

[57] ABSTRACT

Peptide ligands which bind to von Willebrand Factor (vWF) are disclosed. These peptides are selected from the group consisting of RLHSFY, RLKSFY, RLNSFY, RLQSFY, RFRSFY, RIRSFY, RVRSFY, RYRSFY, RLRSFY, HLRSFY, and KLRSFY. The preferred peptide ligand has the sequence RVRSFY. A method of using the disclosed peptides to purify vWF comprises binding the peptides to a support, then passing a solution containing vWF over the supports under condition such that the vWF will selectively bind to the peptides, and then eluting the vWF.

2 Claims, 5 Drawing Sheets

FIG._1

1: ALBUMIN
2: vWF STANDARD
3: AHF FILTRATE (STARTING MATERIAL)
4: MW MARKERS
5: COLUMN FLOW THROUGH
6: LOW SALT WASH
7: HIGH WASH
8: 2% ACETIC ACID ELUATE

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:1:

His Leu Arg Ser Phe Tyr
1                   5

( 2 ) INFORMATION FOR SEQ ID NO:2:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:2:

Lys Leu Arg Ser Phe Tyr
1               5

( 2 ) INFORMATION FOR SEQ ID NO:3:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:3:

Asn Leu Arg Ser Phe Tyr
1               5

( 2 ) INFORMATION FOR SEQ ID NO:4:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:4:

Gln Leu Arg Ser Phe Tyr
1               5

( 2 ) INFORMATION FOR SEQ ID NO:5:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:5:

Arg Leu His Ser Phe Tyr
1               5

( 2 ) INFORMATION FOR SEQ ID NO:6:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:6:

Arg Leu Lys Ser Phe Tyr
1               5

( 2 ) INFORMATION FOR SEQ ID NO:7:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear (i i) MOLECULE TYPE:
    (A) DESCRIPTION: peptide (x i) SEQUENCE DESCRIPTION: SEQ ID NO:7:

Arg Leu Asn Ser Phe Tyr
1               5

(2) INFORMATION FOR SEQ ID NO:8:

(i) SEQUENCE CHARACTERISTICS:
    (A) LENGTH: 6
    (B) TYPE: amino acid
    (C) STRANDEDNESS: single strand
    (D) TOPOLOGY: linear (i i) MOLECULE TYPE:
    (A) DESCRIPTION: peptide (x i) SEQUENCE DESCRIPTION: SEQ ID NO:8:

Arg Leu Gln Ser Phe Tyr
1               5

(2) INFORMATION FOR SEQ ID NO:9:

(i) SEQUENCE CHARACTERISTICS:
    (A) LENGTH: 6
    (B) TYPE: amino acid
    (C) STRANDEDNESS: single strand
    (D) TOPOLOGY: linear (i i) MOLECULE TYPE:
    (A) DESCRIPTION: peptide (x i) SEQUENCE DESCRIPTION: SEQ ID NO:9:

Arg Phe Arg Ser Phe Tyr
1               5

(2) INFORMATION FOR SEQ ID NO:10:

(i) SEQUENCE CHARACTERISTICS:
    (A) LENGTH: 6
    (B) TYPE: amino acid
    (C) STRANDEDNESS: single strand
    (D) TOPOLOGY: linear (i i) MOLECULE TYPE:
    (A) DESCRIPTION: peptide (x i) SEQUENCE DESCRIPTION: SEQ ID NO:10:

Arg Ile Arg Ser Phe Tyr
1               5

(2) INFORMATION FOR SEQ ID NO:11:

(i) SEQUENCE CHARACTERISTICS:
    (A) LENGTH: 6
    (B) TYPE: amino acid
    (C) STRANDEDNESS: single strand
    (D) TOPOLOGY: linear (i i) MOLECULE TYPE:
    (A) DESCRIPTION: peptide (x i) SEQUENCE DESCRIPTION: SEQ ID NO:11:

Arg Val Arg Ser Phe Tyr
1               5

(2) INFORMATION FOR SEQ ID NO:12:

(i) SEQUENCE CHARACTERISTICS:
        (A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:12:

Arg Tyr Arg Ser Phe Tyr
 1               5

(2) INFORMATION FOR SEQ ID NO:13:

(i) SEQUENCE CHARACTERISTICS:
        (A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:13:

Arg Leu Arg Ser Phe Tyr
 1               5

(2) INFORMATION FOR SEQ ID NO:14:

(i) SEQUENCE CHARACTERISTICS:
        (A) LENGTH: 7
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:14:

Arg Val Arg Ser Phe Tyr Lys
 1               5

PEPTIDE LIGANDS WHICH BIND TO VON WILLEBRAND FACTOR

BACKGROUND OF THE INVENTION

1. Field

This invention relates generally to peptide ligands which bind to proteins, and specifically to the use of a peptide ligand to modify a chromatographic substrate for use in affinity purification of proteins such avyon Willebrand Factor.

2. Background

The protein von Willebrand Factor (vWF) is an important cofactor protein in the treatment of hemophilia and related diseases of coagulation. In the blood of a normal person, vWF stabilizes and transports Factor VIII (FVIII), which is directly involved in the blood coagulation cascade. (1) Human deficiency of either vWF or FVIII results in diseases of homeostasis which are treatable with concentrates of the relevant protein or a complex of both. These concentrates are prepared from the pooled blood of a large number of donors and are expensive to produce. Although the concentrates are enriched for the specific factors required, they are still contaminated with other proteins. Also, due to the origin of these concentrates, there is the risk of viral contamination. (2)

The purification of vWF represents a challenge because it is a multimeric protein with molecular weight ranging from 0.5 to 10 million Daltons. (1) This has led to the use of a variety of approaches for this protein, including selective precipitation, size exclusion, ion exchange, or immunoaffinity chromatography steps in purification protocols.

von Willebrand Factor-Factor VIII Complex Concentrates

Preparation of von Willebrand Factor-Factor VIII complex (vWF-FVIII complex) concentrates has been performed classically by precipitation methods from plasma cryoprecipitate. These concentrates are mixtures of vWF-FVIII among many other plasma proteins, especially albumin. Methods rely on differential solubility. Common precipitating agents are metal hydroxides, such as barium hydroxide or aluminum hydroxide, polyethylene glycol, and amino acids, such as glycine. The relevant proteins removed by such procedures are β-globulins and fibrinogen.

More recent isolation methods use ion exchange chromatography to prepare intermediate purity concentrates. FVIII is usually not removed from vWF by this approach. Anion exchange resins have been used to capture vWF-FVIII directly from plasma. (3-4) Purification of vWF-FVIII from cryoprecipitate using anion exchange chromatography has been reported. (5-6) Others have incorporated affinity chromatographic steps in the purification process. (7-10)

Affinity methods have also been introduced for high purity enrichment of vWF-FVIII from plasma, including use of ligands such as lectins (11), and metal chelates. Recently, heparin has been introduced as a ligand for making vWF-FVIII complex concentrate. (12-13)

Important to the present disclosure, Hagen et at. describe purification of either vWF alone or vWF-FVIIIc complex using peptides derived from the amino acid sequence of platelet glycoprotein 1b. (2) They claim purification using any peptide of at least four consecutive amino acids corresponding to amino acids 165-260 of glycoprotein 1b, an integrin receptor for vWF interaction at the platelet surface.

Immunoaffinity chromatography using antibodies to FVIII has been implemented for purification of FVIII, although these preparations are depleted of vWF, for example, in the plasma-derived FVIIIc concentrate Hemofil. (14)

von Willebrand Factor Concentrates

Chromatographic preparation of vWF concentrates devoid of FVIII have also been described. Anion exchange chromatography can be used to separate FVIII from vWF (16–19), typically by including calcium ions at sufficient concentration to disrupt the vWF-FVIII complex.

Immunoaffinity chromatography using antibodies to vWF has been described for making high purity vWF concentrates. (20) Similar antibodies are also used to make high purity FVIII preparations (for example Monoclate) whereby FVIII is released from the vWF bound to antibody by using calcium ions. It is possible to then elute vWF from the antibody adsorbent. However, immunoaffinity chromatography uses monoclonal antibodies as affinity ligands. At present, monoclonal antibodies must be purified extensively prior to use as affinity ligands. Therefore, the process of obtaining FDA (Food and Drug Administration) approval is lengthy and the qualities of the purified proteins may vary. In addition, immobilized antibodies are particularly sensitive to operating conditions. The harsh elution conditions often used in affinity separation processes and sanitation procedures can deplete antibody activity over time.

Peptide Ligand Chromatography

Peptide affinity chromatography using peptides as ligands has advantages over immunoaffinity chromatography (32). One benefit is that peptide ligands consist of only a few amino acids, which, unlike large murine antibodies, are not likely to cause an immune response in case of leakage into the product. Peptide ligands are also much more stable in comparison to antibody ligands. They can be manufactured aseptically in large quantifies under GMP (good manufacturing practices) conditions. The interactions between binding peptides and proteins can be easily modified by synthetic methods to result in mild elution conditions for separation. (32)

The classic affinity interaction involves hydrophilic and hydrophobic interactions at one or several specific locations. (22) Affinity chromatography can be divided into so-called high, or biospecific, affinity chromatography, and weak, or pseudobiospecific, affinity chromatography. These terms describe differences in reversible interactions which are dependent on differences in the nature of ligands. (21) Biospecific affinity ligands depend on interactions between biologically active substances, e.g., an antibody and its antigen, whereas pseudobiospecific ligands are typically small molecules, such as dyes and metal chelates. In both biospecific and pseudobiospecific separations, .the nature of reversible interactions via multiple types of complementary intramolecular bonding are the same. Typically, biospecific interactions have high binding constants, and may have increased specificity.

Peptides can be classified within both biospecific and pseudobiospecific affinity interactions. For example, a peptide sequence may be a subsequence of the interaction site of a protein ligand. This is the case for platelet 1b derived peptides which bind vWF. (2) Specificity may be high, and the protein may be eluted by the peptide. Similarly, a peptide that is without any apparent sequence homology to a biological ligand, still may interact with a ligate, such as the sequence HPQ which mimics biotin and binds streptavidin. (32) Biospecific and pseudobiospecific mechanisms are useful for chromatographic purification of proteins.

Vijayalakshmi (23) demonstrated purification of Factor VIII with vWF attached by using histidyl-Sepharose. The conditions of adsorption suggest that hydrophobic and ionic interactions were important in binding. For example, the pH of adsorption was 6.0 (range 5.8–6.1) at low ionic strength. The pI of vWF is 5.8, and at this pH the interactions may not be solely ionically driven. Desorption was accomplished using 0.1M glycine, 0.3M lysine and 0.3M $CaCl_2$, conditions useful for interfering with ionic interactions. The authors also demonstrated that the histidine-Sepharose system was useful for other separations, including binding IgG, and endotoxin.

Peptide ligands can be found by screening phage peptide libraries. (24) Phage peptide libraries are created by the insertion of a random gene of a given length into bacterial phages which are cultivated for the expression of random peptides on the phage surfaces. Millions of phage particles, each with a different peptide, are then incubated with target protein mobilized on a Petri dish. Phage particles that are not bound specifically to the target protein are washed away. The specifically retained phages are used to infect E. coli cells for gene amplification. The amplified gene can be sequenced and the specific peptide sequence deduced.

SUMMARY OF THE INVENTION

Here we describe a group of peptide affinity ligands that fall into the broad classification of pseudobiospecific ligands which bind to vWF. This group includes the following peptide affinity ligands: RLHSFY, RLKSFY, RLNSFY, RLQSFY, RFRSFY, RIRSFY, RVRSFY, RYRSFY, RLRSFY, HLRSFY, and KLRSFY. The preferred ligand is RVRSFY. Furthermore, we describe a method of purifying vWF which comprises passing a protein containing solution over a substrate which has bound upon it a peptide affinity ligand of the defined sequence, and then eluting the vWF.

SPECIFIC EMBODIMENTS

Materials and Methods

Amination of Resin and Solid Phase Peptide Synthesis

Toyopearl® 650M chelate resin from TosoHaas (Montgomeryville, Pa.) was chosen for the amination and direct synthesis of peptides. The resin was rinsed in a 25 g reaction vessel with water, methanol and dimethylformamide (DMF, Burdick & Jackson). A five-fold molar excess over resin carboxylate of ethylenediamine (Aldrich, Milwaukee, Wis.) was coupled onto the carboxylate moiety with a slight molar excess of benzotriazole-1-yl-oxy-trispyrrolilidinophosphonium (PyBOP, Nova Biochem, La Jolla, Calif.) and N-methylmorpholine (NMM, three fold molar excess over PyBOP, Aldrich) in DMF for 60 minutes. This aminated resin was washed with DMF, then methanol, then dried in-vacuo. To generate non-cleavable peptideresins, two beta-alanine (Nova Biochem) spacer residues were coupled by standard solid phase peptide synthesis couplings.

Peptides were synthesized by the solid phase method on a Gilson AMS422 Multiple Peptide Synthesizer (Middleton, Wis.) utilizing FMOC (9-fluorenylmethoxycarbonyl) as the α-amino protection. Briefly, each amino add (5-fold molar excess; 1 ml of 0.5M in DMF) was activated in-situ with PyBOP (0.5 ml of 0.3M in DMF) and NMM (0.25 ml of 1.19M in DMF) with our modified TosoHaas resin (0.3 g, 120 µmoles) or Rink amide resin (Nova Biochem, 0.5 g, 200µ). Coupling was allowed to proceed with argon-bubbling agitation for 45 minutes. All peptides were cleaved and/or deblocked with Reagent R (5 ml of 90% Trifluoroacetic acid (TFA), 5 % thioanisole, 3% ethanedithiol, 2% anisole, all from Aldrich) for 3.5 hours. The TosoHaas resin-peptides were deprotected in the synthesis vessel, extensively washed with methanol and dried in-vacuo. The peptide mixtures from Rink resin were filtered away from resin directly into 40 ml cold anhydrous diethyl ether (Aldrich) through a medium porosity sintered glass funnel. The filter cakes were dissolved in 50% acetonitrile/water and lyophilized in a tared scintillation vial. These precipitated, unpurified peptides were dissolved at 25–50 mg/ml in 50% acetonitrile/water and 1 ml was purified by preparative HPLC (Gilson, Inc. Middleton, Wis.) with a 22 mm×250 mm (C18 15µ 300 Å, Vydac, Hesperia, Calif.) reversed phase column. The analytical HPLC system, Ultrafast Microprotein Analyzer, was purchased from Michrom BioResources, Inc. (Sacramento, Calif.). Molecular weights and sequences of peptides were verified by MS/MS determinations using fast atom bombardment mass spectrometry on a JEOL HX110HF instrument.

Peptide immobilization and affinity column packing

Purified peptides were dissolved in 0.2M sodium bicarbonate and 0.5M NaCl at pH 10.3. Resin powder, Toyopearl-Epoxy-650M (TosoHaas, Montgomeryville, Pa.), was directly mixed with peptide solution at the ratio of 0.5 g resin to 3.2 ml peptide solution. The slurry was rotated at 40° C. for 24 hours, then the solution was separated from the resin. Peptide concentrations in the solution before and after immobilization were determined by analytical C18 reversed phase chromatography. Since there was no dilution effect when the Toyopearl powder was mixed with the peptide solution, the decrease of peptide peak area after mixing was due to immobilization and was used to calculate the peptide coupling efficiency. The final peptide density on the resin could be deduced.

After peptide coupling, the reactive sites on the gel were blocked by reacting with 1M ethanolamine at pit 11 for 24 hours at 40° C. The gel was washed with degassed PBS (phosphate buffered saline) buffer and 1M sodium chloride at pH 7.4.

The gel slurry (1 ml wet gel mixed with 2 ml degassed PBS and 1 M sodium chloride buffer) was transferred into a packing device (from PerSeptive Biosystems, Framingham, Mass.) and packed into a PEEK column (0.75 cm×5 cm from Alltech, Deerfield, Ill.) at a flow rate of 8 ml/min. The pressure drop was 60 psi, which was within the maximum pressure drop of 120 psi suggested by the manufacturer. The column was washed with at least 4 bed volumes of binding buffer (10 mM HEPES, 100 mM NaCl, 5 mM calcium chloride at pH 7) and elution buffer (2% acetic acid), then equilibrated with binding buffer.

Treatment with solvent and detergent

The starting material called PEG filtrate was processed from human plasma cryoprecipitate at Bayer Corp. (Clayton, N.C.). This material contained vWF, FVIII, significant fibrinogen, fibronectin, and IgM. The PEG filtrate was treated with 1% TNBP (tri-n-butylphosphate) and 0.5 % Tween 20 (from Aldrich) at 30° C. for 3 hours. After the treatment, the mixture was directly injected onto peptide affinity columns.

ELISA

Protein concentrations were monitored by $A_{280}$ absorbance. Samples were characterized using vWF ELISA. Briefly, anti-vWF antibody (from Accurate Inc. N.Y.) was coated on each well of a microliter plate (96 wells from Corning, N.Y. 14831) overnight using 100 µl solution of antibody diluted 200 times in 0.1M sodium bicarbonate buffer at pH 9.6. Each well was then blocked with 300 µl solution of 1% BSA in PBS for 1 hour at room temperature. The plate was washed 5 times with PBS. Pure vWF and the collected samples were diluted to a concentration range between 0.02 to 0.2 µg/ml using 1 mg/ml BSA in PBS. Each sample (100 µl) was incubated with the anti-vWF coated well for 1 hour at room temperature and the plate was washed 5 times with PBS plus 0.1% Tween 20. A second anti-vWF antibody with horse radish peroxidase (HRP) conjugate (from DAKO, Glostrup, Denmark) at a concentration of 1 to 500 dilution was introduced to each well and incubated for i hour at room temperature. The plate was washed again with PBS plus 0.1% Tween 20 for 5 times. Substrate ABTS (2,2'-azino-bis(3-ethylbenz-thiazoline-6-sulfonic acid)) and $H_2O_2$ were used for the kinetic reading at 410 nm using Bio Kinetics Reader from BioTek (Winooski, Vt.).

Gel electrophoresis

The molecular weights and purity of the collected samples were determined by SDS-PAGE under reducing conditions using Phastsystem from Pharmacia (Piscataway, N.J.). To determine the multimers of vWF, 1.5% agarose gel electrophoresis was used. The agarose gel electrophoresis was performed on the BioRad mini gel system.

Adsorption isotherm measurements

Adsorption isotherms were measured in a batch mode. In a siliconized microcentrifuge tube, 0.1 ml wet gel was mixed with vWF solution of 10 mM HEPES, 5 mM calcium chloride and 0.5M sodium chloride at pH 7 in a total volume of 0.3 ml. The microcentrifuge tube was incubated at 25° C. for 20 minutes, then the gel was separated from the solution by microcentrifugation. The concentrations of vWF in solutions were measured both by absorbance at 280 nm with an extinction coefficient of 1.2 for 1 mg/ml vWF and by ELISA.

Materials

Highly purified vWF derived from human plasma was from Bayer Corp. (Berkeley, Calif.). Koate® containing vWF, FVIII, and albumin was a product of Bayer Corp. (Clayton, N.C.). Other chemicals used in our experiment were from Sigma in analytical grade or purer. All aqueous solutions were prepared using deionized water purified by Barnstead nanopure water purification system (Dubuque, Iowa).

BEST MODE FOR CARRYING OUT THE INVENTION

In order to discover the best mode of practicing the invention, we investigated the effects of peptide sequence, peptide density, salt concentration, temperature, solvent hydrophobicity, and solvent pH on the efficiency of purification.

Identifying peptides that bind to vWF

Peptides which bind to vWF were discovered by screening a random 6-mer bacteriophage display library with purified vWF depleted of Factor VIII. Clones selected for vWF binding were subjected to standard DNA sequence analysis to deduce the corresponding peptide sequence. Peptides of the corresponding sequence were synthesized chemically, coupled to resin, and screened for their ability to bind vWF. The peptide RLRSFY (SEQ ID NO: 13) was deduced from the selection protocols and tested for utility as an affinity ligand. For convenience, amino acids are referred to by their conventional abbreviations as set forth in Lehninger. (31)

Figure 1:
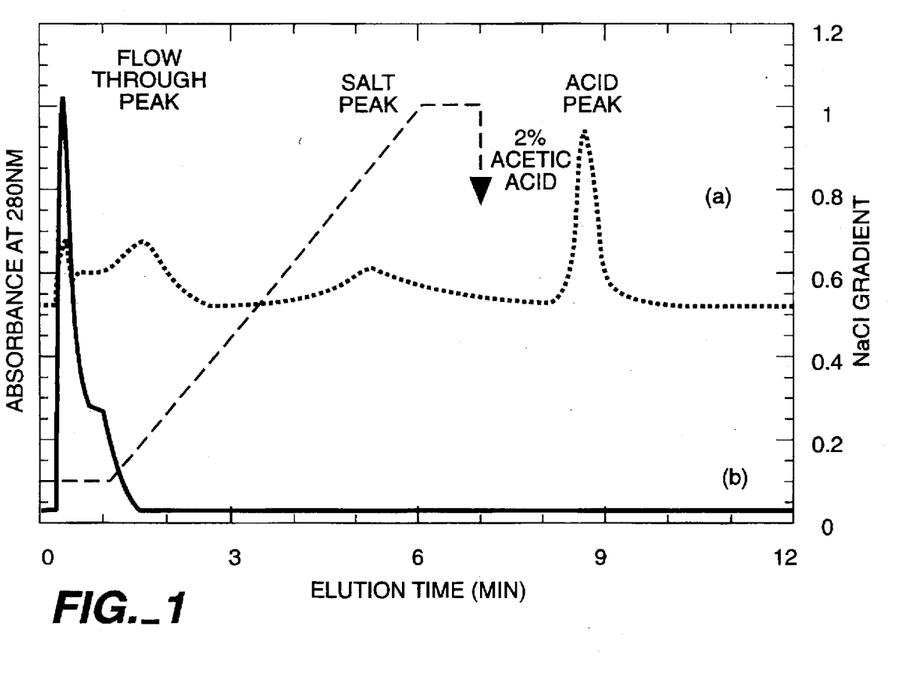
FIG. 1 shows the elution profiles for Koate® Factor VIII from columns with (a) and without (b) peptide RLRSFY (SEQ ID NO:13).

Affinity chromatography for the purification of vWF using immobilized peptide RLRSFY Peptide RLRSFY was directly synthesized (25) onto a modified Toyopearl resin (—(β-Ala)$_2$-Toyopearl) and the resin was packed in a 1 ml column (0.7×2.5 cm). Koate (Bayer's product containing vWF, FVIII and human albumin) was applied to the column at a flow rate of 2 ml/min in binding buffer (10 mM HEPES, 5 mM calcium chloride and 0.1M NaCl, pH 7). After 1 min of washing in binding buffer, a linear gradient from 0.1 to 1M NaCl in HEPES buffer was applied to the column over 5 min. The elution with high salt concentration was maintained for another 1 min, before 2% acetic acid was used to elute the retained protein. The chromatogram is shown in FIG. 1. When 0.1 ml Koate was applied to the column, about 60% of the protein did not bind to the peptide resin or was loosely bound and eluted by sodium chloride. The remainder was eluted using 2% acetic acid. In a control experiment in which no peptide was attached to the resin (only —(β-Ala)$_2$-Toyopearl, almost all protein from 0.1 ml Koate flowed through the column under the same conditions used for the peptide-Toyopearl column. This chromatogram is also shown in FIG. 1.

The peaks in FIG. 1 were collected and analyzed for vWF by ELISA and purity by SDS-PAGE. Most of the vWF was retained by RLRSFY-Toyopearl column and could not be eluted by sodium chloride up to 1M (Table 1). Approximately one-half of vWF was recovered in the acid peak. In comparison, 83% of total vWF was found in the flow through peak from the (β-Ala)$_2$-Toyopearl column.

Table 1 also shows that total protein (represented as absorbance at 280 nm, $A_{280}$) recovered from the two columns are similar. Only one-half of the applied vWF is recovered from the peptide-Toyopearl column. This suggests that acid denatures a portion of the vWF during elution. This is confirmed by direct acid treatment then neutralization of vWF standards on the ELISA assay (data not shown).

Analyses of the column fractions by SDS-PAGE (reducing) revealed that the major protein in the acid eluate from the peptide-Toyopearl had a subunit molecular weight of 225 kDa. In the acid peak, the gel also showed a small amount of albumin at 66 kDa position (data not shown). We concluded that the peptide-Toyopearl resin could retain vWF from the Koate mixture, but some modification on the peptide sequence might increase selectivity. That led to the following studies of sequence optimization.

TABLE 1

Mass balances based on $A_{280}$ and ELISA measurements

| Samples | RLRSFY-Toyopearl | | ($\beta$-Ala)$_2$-Toyopearl | |
|---|---|---|---|---|
| | $A_{280}$ | % vWF activity by ELISA | $A_{280}$ | % vWF activity By ELISA |
| input sample | 7.8 (0.1 ml) | | 7.8 (0.1 ml) | |
| flow through | 0.071 (×4 ml) | 1.6 | 0.185 (×4 ml) | 83.32 |
| salt | 0.014 (×12 ml) | 0.09 | 0.002 (×12 ml) | 0.9 |
| acid | 0.070 (×4 ml) | 49.78 | 0.003 (×4 ml) | 0.06 |
| % recovery | 95% | | 98% | |

Sequence Optimization

Single conservative amino acid substitutions at the first three positions of RLRSFY were synthesized directly on ($\beta$-Ala)$_2$-Toyopearl. Amino acid substitutions used for both positions of arginine (R) were histidine (H), lysine (K), glutamine (Q), and asparagine (N). Substitutions for leucine (L) include isoleucine (I), valine (V), phenylalanine (F), and tyrosine (Y). These individual substitutions created 12 unique peptide sequences. (SEQ ID NOS: 1 to 12) After the resins were packed into 1 ml glass columns, 0.1 ml Koate was applied to each column and eluted with sodium chloride gradient and 2% acetic acid, same as in FIG. 1. Fractions were collected and analyzed for $A_{280}$ absorbance and ELISA. The results are listed in Table 2. It is evident that when the R at the N-terminus was replaced by N or Q, the percentage of vWF captured by the column was significantly reduced. The substitution of the R at the third position from the N-terminus had no effect on the capture of vWF from Koate. This seemed to suggest that the R at the N-terminal played a more important role than the R at third position in the capture of vWF from Koate. Maximum vWF binding occurred when L was substituted for V.

Figure 2:
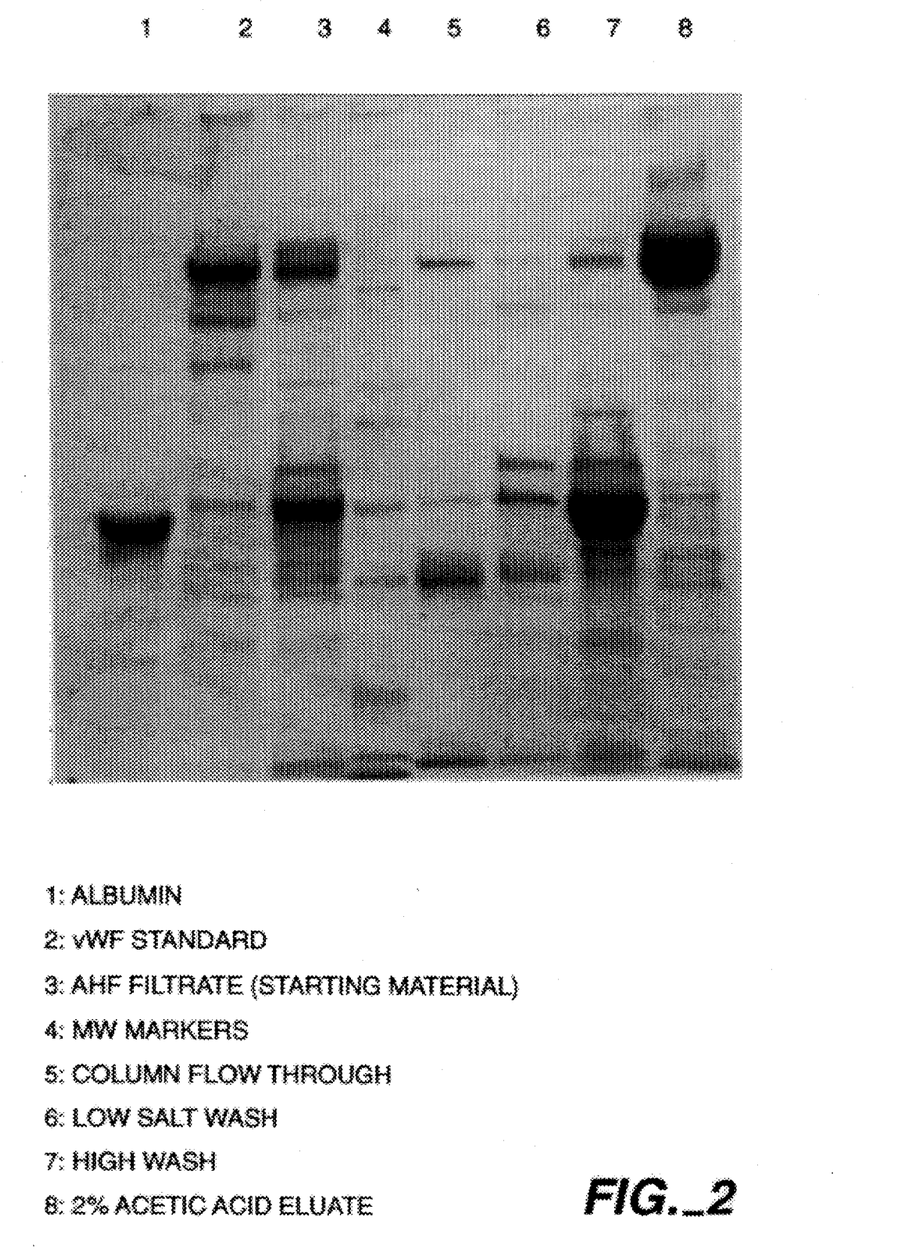
FIG. 2 shows the SDS-PAGE of fractions collected from the chromatography using column RVP-SFY-Toyopearl® Resin. (SEQ ID NO: 11) Lane 1: human serum albumin standard; lane 2: standard vWF; lane 3: starting material (PEG filtrate); lane 4: molecular weight standard; lane 5: flow through peak; lane 6: 0.15M NaCl eluate peak; lane 7:0.35M NaCl eluate peak; lane 8:2% acetic acid eluate peak.

Confirmation of the purification of vWF on RVRSFY-Toyopearl was performed using PEG filtrate as the starting material (FIG. 2). Inclusion of a 0.15M NaCl wash and an additional 0.35M NaCl wash removed the bulk of the albumin. Bound vWF was eluted with 2% acetic acid. As seen in FIG. 2, lane 8, vWF was highly purified by binding to RVRSFY-Toyopearl.

TABLE 2

Comparison of vWF capture from different peptide-Toyopearl resins

| Peptide Resins | SEQ ID NO. | % area of acid peak | % vWF by ELISA | | |
|---|---|---|---|---|---|
| | | | flow through | salt | acid |
| HLRSFY | 1 | 26.7 | 0.75 | 0.28 | 32.7 |
| KLRSFY | 2 | 27.1 | 1.03 | 9.83 | 26.94 |
| NLRSFY | 3 | 14.8 | 19.96 | 11.88 | 6.98 |
| QLRSFY | 4 | 9.2 | 29.45 | 11.69 | 2.20 |
| RLHSFY | 5 | 24.9 | 1.77 | 2.89 | 50.72 |
| RLKSFY | 6 | 25.1 | 0.60 | 3.59 | 45.58 |
| RLNSFY | 7 | 24.5 | 0.26 | 1.50 | 47.68 |
| RLQSFY | 8 | 20.1 | 0.46 | 0.54 | 50.68 |
| RFRSFY | 9 | 27.8 | 0.20 | 0.07 | 47.96 |

TABLE 2-continued

Comparison of vWF capture from different peptide-Toyopearl resins

| Peptide Resins | SEQ ID NO. | % area of acid peak | % vWF by ELISA | | |
|---|---|---|---|---|---|
| | | | flow through | salt | acid |
| RIRSFY | 10 | 28.0 | 1.92 | 4.09 | 44.78 |
| RVRSFY | 11 | 30.2 | 0.09 | 0.08 | 55.78 |
| RYRSFY | 12 | 27.1 | 1.65 | 0.14 | 51.72 |

Adsorption isotherm of vWF to RVRSFY-Toyopearl

Interactions between RVRSFY directly synthesized on Toyopearl and vWF were studied through adsorption isotherm measurements. Because vWF consists of a wide range of molecular weights, complex theoretical analyses are required to obtain binding constants from the adsorption isotherms. In addition, different multimers of vWF may have different binding constants. To simplify the analyses, vWF with molecular weight around 1000 kDa was fractionated from Koate using size exclusion chromatography with Bio-Gel A-5M gel (BioRad) and analyzed by nonreducing agarose gel electrophoresis.

Figure 3:
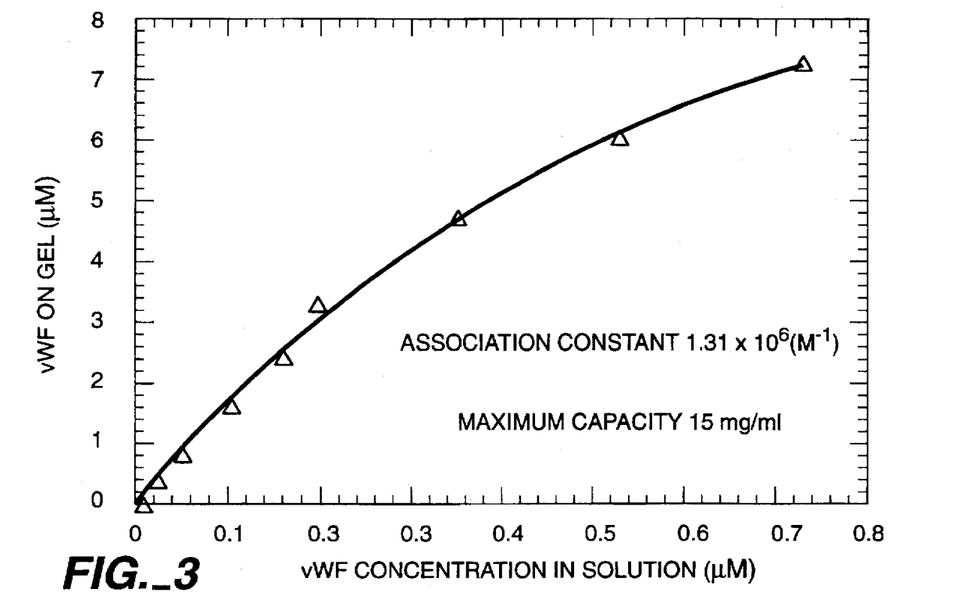
FIG. 3 shows the adsorption isotherm of vWF onto the RVRSFY-Toyopearl. (SEQ ID NO:11)

The adsorption isotherm in FIG. 3 shows that at a given concentration of vWF, most of the vWF was adsorbed to the RVRSFY-Toyopearl. The adsorption isotherm was fitted using the Langmuir equation, resulting in an association constant of $1.31 \times 10^6$ ($M^{-1}$). The curve fit also showed that the maximum capacity of the resin was 15 mg vWF/ml resin, or approximately 60 mg vWF/g resin.

The effect of peptide density on the adsorption isotherms

The peptide Ac-RVRSFYK-amide (SEQ ID NO: 14) was chemically synthesized and mobilized to the Toyopearl-Epoxy-650M resin through the C-terminal lysine. The acetyl group at the N-terminus prevented the peptide from coupling to the resin at the N-terminal amine. Peptide coupling efficiency and peptide density on the resin were monitored by reversed-phase HPLC. The coupling efficiencies were in the range of 95 to 75% corresponding to 5 to 60 mg peptide/ml.

Figure 4:
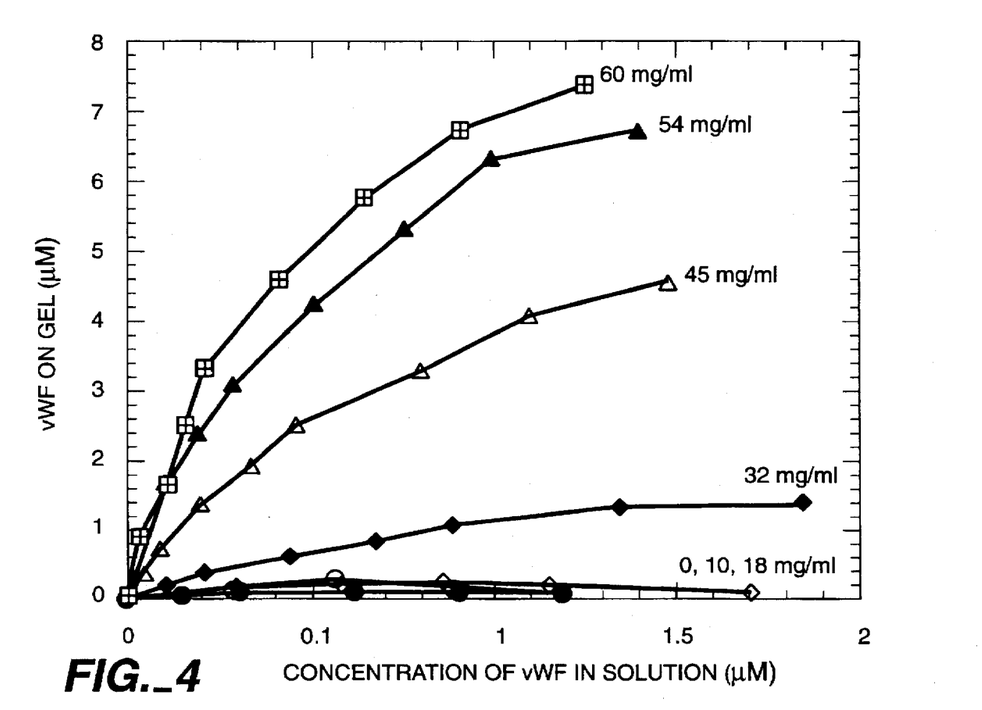
FIG. 4 shows the effect of peptide density on the adsorption of vWF to Ac-RVRSFYK-Toyopearl. (SEQ ID NO:14)

The effect of peptide density on the adsorption isotherms is shown in FIG. 4. An increase of peptide density increases adsorption of vWF. A minimum peptide density, 32 mg peptide Ac-RVRSFYK/ml resin (32 μmol/ml), is required for the binding of vWF to the peptide. The Langmuir equation was used to fit these isotherms, and the association constants and maximum capacities obtained from curve fits are listed in Table 3. They show an increase of association constant and maximum binding capacity with an increase of peptide density mobilized on the Toyopearl resin.

TABLE 3

Effect of peptide density on the association constant and maximum capacity.

| Peptide density mg/ml | Association constant M-1 | Maximum capacity mg/ml |
|---|---|---|
| 32 | $8.82 \times 10^5$ | 2.32 |
| 45 | $1.12 \times 10^6$ | 7.3 |
| 54 | $1.68 \times 10^6$ | 9.7 |
| 60 | $2.06 \times 10^6$ | 10.33 |

Figure 5:
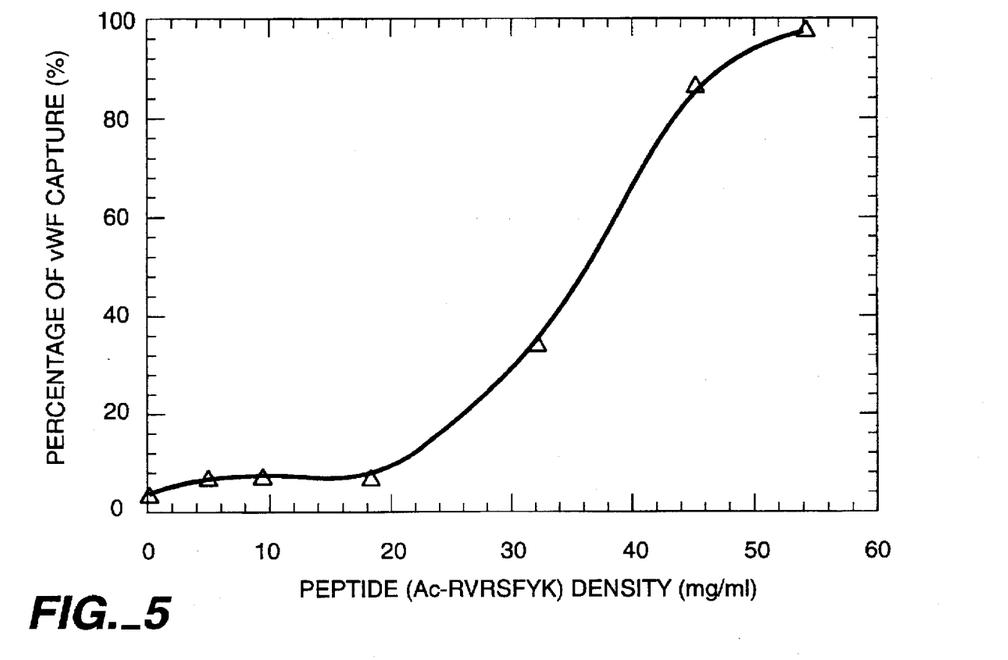
FIG. 5 shows the effect of peptide density (on Ac-RVRSFYK-Toyopearl (SEQ ID NO: 14)) on the separation of vWF from Koate.
Figure 6:
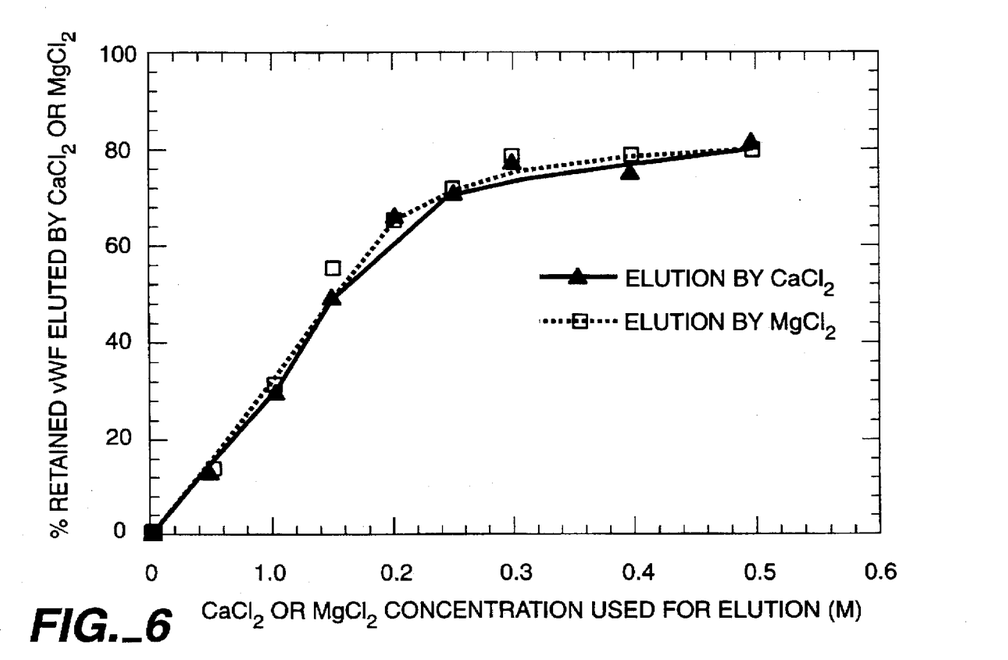
FIG. 6 shows the effect of divalent cation concentration on the elution of captured vWF from column packed with 55 mg/ml Ac-RVRSFYK-Toyopearl. (SEQ ID NO: 14)

When the immobilized peptide resins were packed in columns for the separation of vWF from Koate, the percentage of vWF in Koate captured by columns were also dependent on the peptide density. FIG. 5 shows the effect of peptide density on the capture of vWF from Koate in the chromatography format. When the peptide density was less than 32 mg/ml, almost no capture of vWF was obtained. With an increase of peptide density, the capture of vWF went through a transition from no capture to almost complete capture at 54 mg/ml density. This trend was consistent with that obtained from the adsorption isotherm measurements. The effects of salts and temperature on the elution of captured vWF from peptide-Toyopearl column Generally, elution with high salt concentration can recover proteins with higher biological activities than acid elution. For this reason, the salt concentration for elution was increased to 2M NaCl, but the captured vWF from Koate by the Ac-RVRSFYK-Toyopearl was not released. When divalent salts, such as $CaCl_2$ and $MgCl_2$ were used for elution, most of the captured vWF by the peptide column was released. FIG. 6 shows the dependence of the elution of retained vWF on calcium and magnesium concentrations. When calcium and magnesium concentrations were higher than 0.3M, about 80% of captured vWF could be eluted.

At elevated temperatures, calcium was more efficient in eluting the captured vWF from a column packed with Ac-RVRSFYK-Toyopearl. For example, when the temperature was increased from 22° to 26° and 30° C., the percentage of vWF eluted by 0.5M calcium chloride solution increased from 80% to 85% and 89%, respectively. The efficient elution of the captured vWF by divalent salts and by increasing temperature indicates that ionic interactions between immobilized peptide and vWF may play an important role in the binding interaction.

In order to make sure that the higher temperature did not damage vWF and to examine vWF recovery from calcium chloride elution, vWF was separated from 0.1 ml Koate using 0.4 ml column containing 54 mg/ml peptide Ac-RVRSFYK. The fractions of flow through, salt (1M NaCl), 0.5M $CaCl_2$, and 2% acetic acid elutions were collected and vWF activity in each fraction was measured by ELISA. The $CaCl_2$ fraction contained 82.5% of total vWF, and the vWF recovered in all fractions was 87.8%. In comparison, when only 2% acetic acid was used for elution, 55.9% of total vWF was recovered (Table 2).

The effect of solution pH on the capture of vWF from Koate

Figure 7:
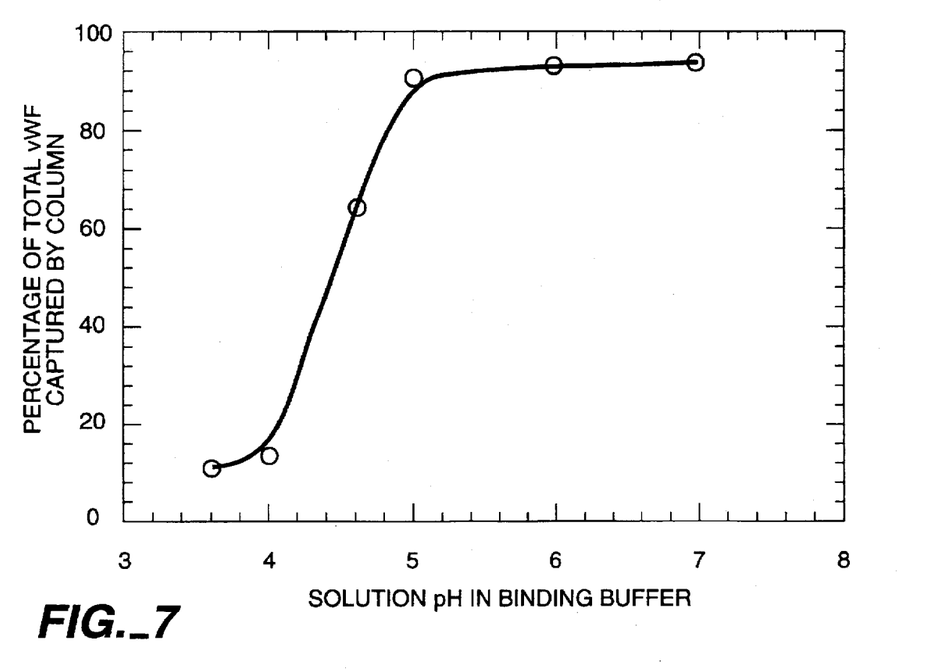
FIG. 7 shows the effect of solution pH on the capture of vWF from Koate using Ac-RVRSFYK-Toyopearl. (SEQ ID NO:14)

Ionic interactions between ligands and proteins normally diminish when the solution pH changes from above (or below) to below (or above) isoelectric points of proteins. In the case of immobilized Ac-RVRSFYK on Toyopearl, the ligand is positively charged at any pH lower than 12. Solution pH higher than 5.8, the isoelectric point for vWF (27), is expected to have a favorable interaction because vWF is negatively charged. As shown in FIG. 7, between pH 6 and 7, about 95% of vWF was captured by the peptide column. However, when the solution pH was 5 and 4.6, significant percentages (91% and 65% respectively) of vWF were captured by the peptide, as shown in FIG. 7. These results suggest that at low pH, ionic interaction is not the only force involved in the capture of vWF.

EXAMPLE

The purification of vWF from cryoprecipitate PEG filtrate of human plasma

Figure 8:
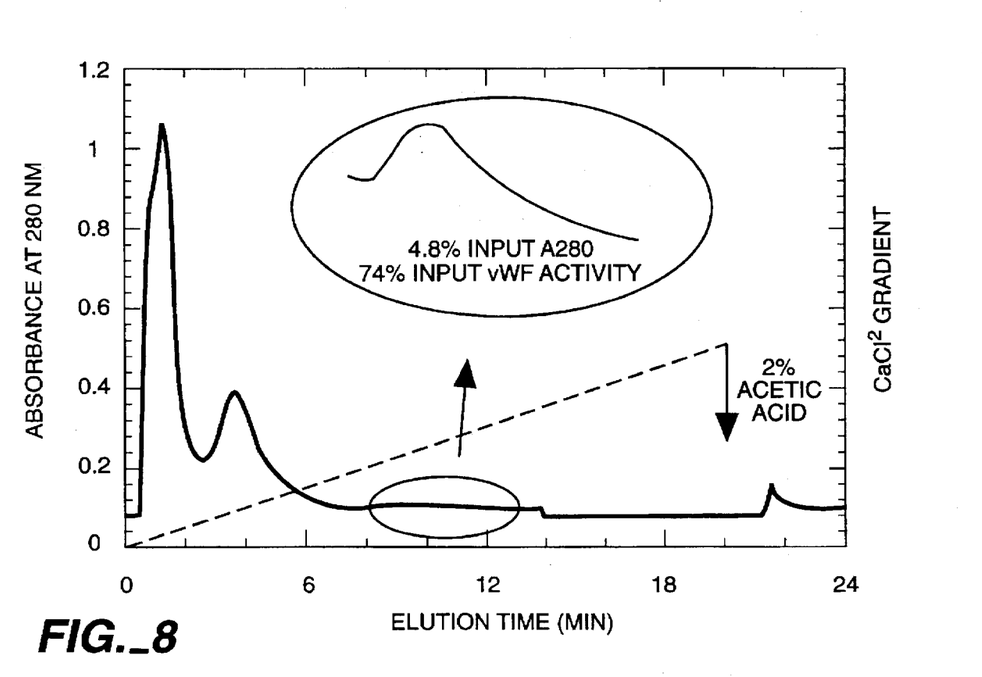
FIG. 8 shows the purification of vWF from crude material PEG fitrate in the cryoprecipitate of human plasma using Ac-RVRSFYK-Toyopearl. (SEQ ID NO: 14)

Crude PEG fitrate from the cryoprecipitate of human plasma was used to demonstrate a practical separation. The PEG filtrate was treated with virus inactivation reagents, 1% TNBP and 0.5% Tween 20 at 30° C. for 3 hours. The treated PEG fitrate was injected directly into the column. As shown in FIG. 8, vWF in the PEG fitrate was captured and resolved using a calcium gradient from 5 mM to 500 mM using a column containing 54 mg/ml peptide Ac-RVRSFYK-Toyopearl. Approximately 74% of the total vWF was eluted with 0.35M $CaCl_2$ (small peak at 10 min).

CONCLUSION

We have described peptides selected from a peptide library for use as affinity ligands for vWF purification. Measurements of the association constant of vWF to mobilized peptides reveal that the attachment of vWF to the surface is multimeric. An increase of peptide density was noted to increase the binding constant and maximum capacity (FIGS. 4, 5). Such phenomena are characteristics of multipoint interaction because an increase of ligand density will increase the possibility of interaction between immobilized ligand and protein. (29) Finally, the purification of vWF from a crude PEG filtrate of human plasma by affinity chromatography was demonstrated.

The peptide RVRSFY, and also RLRSFY and other small peptides of similar sequence, fall into the broad classification of pseudobiospecific ligands which have an affinity for vWF. In this case the interactions appear to be strong, and specificity is intermediate. The mechanism of binding appears to be a mixed-mode, i.e., a combination of different types of bonding, a basic necessity for all affinity interactions. Ionic interactions through the arginine guanidinium group at the N-terminus are important. The N-terminal primary amine, on the other hand, is unimportant. Thus other interactions play a part, such as hydrophobic bonding to the aliphatic or aromatic amino acids in the peptide.

The use of small peptides to purify vWF has previously been reported by Hagen et at. (2) The method described by Hagen et al. uses peptides derived from the sequence of platelet glycoprotein 1b. Analysis of residues 165–260 of glycoprotein 1b reveals no similarities to any of the peptides disclosed in the present invention. Furthermore, a Protein Database search conducted on the peptides revealed homologous sequences in only three proteins, none of which are associated with vWF or platelet glycoprotein 1b. (The proteins with homologous sequences were genome polyprotein 1 from grapevine chrome mosaic virus, ribosomal protein L5 from *Euglena gracilis*, and a probable sulfate transport protein YBR294w in yeast.)

In conclusion, we have demonstrated the use of novel peptides derived from peptide libraries for the affinity purification of proteins, where the peptides are directly synthesized or immobilized on an affinity matrix. The conservative substitution of peptide sequence is a useful technique for the modification of selectivity. Finally, peptide density, solution pH, and salt concentration can be controlled to optimize the separation of vWF from crude material PEG filtrate in the cryoprecipitate of human plasma.

The above examples are intended to illustrate the invention and it is thought variations will occur to those skilled in the art. Accordingly, it is intended that the scope of the invention should be limited only by the claims below.

REFERENCES

1. Ruggeri, Z. M. & Ware, J., *Thromb. Haemost.* 67:594–599 (1992).
2. Kumar, A. A. et al., U.S. Pat. No. 5,200,510, Apr. 6, 1993, Assignee: Zymogenetics.
3. Bos et al., *Thromb. Haemost.* 65:1160 (1991).
4. The & Froget, *Vox Sang.* 67:8–13 (1994).
5. Austen & Smith, *Thromb. Haemost.* 48:46–48 (1982).
6. Harrison et al., *Thromb. Res.* 50:295–304 (1988).
7. Te Booy etal., *Thromb. Haemost.* 61:234–237 (1989).
8. Te Booy etal., *J. Chromatogr.* 503:103–114 (1990).
9. Burnouf etal., *Vox Sang.* 60:8–15 (1991).
10. Josic etal., *J. Chromatogr.* 662:181–190 (1994).
11. Zhou et al., *Protein Expr. Purif.* 5:138–143 (1994).
12. Bhattacharya et al., U.S. Pat. No. 5,110,907, May 5, 1992, assignee: Alpha Therapeutic Corp.
13. U.S. Pat. No. 5,288,853, assignee: Alpha Therapeutic Corp.
14. Griffith, Ann. *Hematol.* 63:131–137 (1991).
15. Addiego etal., *Thromb. Haemost.* 67:19–27 (1992).
16. Burnouf-Radosevich & Burnouf, *Vox Sang.* 62:1–11 (1992).
17. Goudemand et al., *Br. J. Haematol.* 80: 214- (1992).
18. Arrighi, et al., *Vox Sang.* 64:13–18 (1993).
19. Josic et al., *J. Chromatogr.*, 662:181–190 (1994).
20. Farb & Newman, U.S. Pat. No. 5,006,642, Apr. 9, 1991, assignee: Rhone-Poulenc Rhorer Pharmaceuticals
21. Sundaram & Yarmush, *Biotechnology*, 2d ed., 3:643–677 (1993).
22. Dean, P. D. G. et al., *Affinity Chromatography—A Practical Approach*, IRL Press (1985).
23. Vijayalakshmi, M. A., The case of immobilized histidine as a universal ligand, in *Molecular Interaction in Bioseparations*, T. T. Ngo, ed., Plenum Press, New York, pp. 257–275 (1993).
24. Smith, G. P. et al., *Gene* 128:37 (1993).
25. Buettner, J. A. et al., *Internat'l J. Pept. Prot. Res., in press* (1995).
26. Janson, J.-C. & Ryden, L., *Protein Purification Principles, High Resolution Methods, and Applications*, VCH Publishers, Inc., New York (1989).
27. Human Protein Dam, A. Haeberli, ed., VCH Publishers, Inc., New York (1992).
28. Hayzer, D. J. & Jaton, J.-C., in *Methods in Enzymology*, G. DiSabato et al., eds., Academic Press, Orlando, pp. 26–37 (1985).
29. Boyer, P.M. & Hsu, J. T., *Chem. Eng. Sci.* 47:241–251 (1992).
30. Kyte, J. & Doolittle, R. F., *J. Mol. Biol.* 157:105–132 (1982).
31. Lehninger, Albert L., *Biochemistry*, 2d ed., Worth Publishing, New York, p. 72 (1975).
32. Baumbach, G. A. & Hammond, D. J., *BioPharm* 5:24–35 (1992)

What is claimed is:

1. A composition comprising a defined sequence of six consecutive amino acid residues, wherein the defined sequence is selected from the group consisting of RLHSFY, RLKSFY, RLNSFY, RLQSFY, RFRSFY, RIRSFY, RVRSFY, RYRSFY, RLRSFY, HLRSFY, and KLRSFY.

2. A method of purifying von Willebrand factor comprising contacting a solution containing von Willebrand factor with a substrate comprising an amino acid sequence selected from the group consisting of RLHSFY, RLKSFY, RLNSFY, RLQSFY, RFRSFY, RIRSFY, RVRSFY, RYRSFY, RLRSFY, HLRSFY, and KLRSFY under conditions sufficient to bind von Willebrand factor to the substrate.

* * * * *